US010393639B2

(12) United States Patent
Iglseder

(10) Patent No.: US 10,393,639 B2
(45) Date of Patent: Aug. 27, 2019

(54) METHOD AND SYSTEM FOR SIMULTANEOUSLY MEASURING FINE PARTICLE CONCENTRATIONS PM1, PM2.5 AND PM10—PARTICULATE MATTER

(71) Applicant: Heinrich Iglseder, Rodenberg (DE)

(72) Inventor: Heinrich Iglseder, Rodenberg (DE)

( * ) Notice: Subject to any disclaimer, the term of this patent is extended or adjusted under 35 U.S.C. 154(b) by 0 days.

(21) Appl. No.: 15/528,611

(22) PCT Filed: Nov. 20, 2015

(86) PCT No.: PCT/EP2015/002326
§ 371 (c)(1),
(2) Date: Jul. 13, 2017

(87) PCT Pub. No.: WO2016/078768
PCT Pub. Date: May 26, 2016

(65) Prior Publication Data
US 2017/0336313 A1  Nov. 23, 2017

(30) Foreign Application Priority Data
Nov. 21, 2014  (DE) .......................... 10 2014 017 220

(51) Int. Cl.
*G01N 15/06*  (2006.01)
*G01N 15/02*  (2006.01)
*G01N 15/00*  (2006.01)

(52) U.S. Cl.
CPC .......... *G01N 15/06* (2013.01); *G01N 15/0205* (2013.01); *G01N 15/0211* (2013.01);
(Continued)

(58) Field of Classification Search
CPC ........ G01J 1/429; G01J 1/0407; G01J 1/0418; G01J 1/26; G01J 1/4257; G01J 1/58;
(Continued)

(56) References Cited

U.S. PATENT DOCUMENTS

| 3,787,122 A | 1/1974 | Lepper, Jr. |
| 2003/0090656 A1 | 5/2003 | Ikeda et al. |

(Continued)

FOREIGN PATENT DOCUMENTS

| EP | 1158292 | 11/2001 |
| WO | 2013022971 | 2/2013 |

OTHER PUBLICATIONS

Thompson, Michael, "Nephelometer Operating Procedure Air Quality Program", Dec. 1, 2008, pp. 1-20, Department of Ecology State of Washington, Publication 01-02-001 (rev.Dec. 2008), https://fortress.wa.gov/ecy/publications/publications/0102001.pdf.

Riefler, Norbert et al., "Intercomparison of Inversion Algorithms for Particle-Sizing Using Mie Scattering", Particle and Particle System Characterization, vol. 25, No. 3, Sep. 1, 2008, pp. 216-230.

(Continued)

*Primary Examiner* — Michael P Stafira
(74) *Attorney, Agent, or Firm* — Volpe and Koenig, P.C.

(57) ABSTRACT

A method for measuring, in particular simultaneously measuring, different particle concentrations, in particular particulate matter concentrations, preferably in a flow, using a particle measuring system, in particular a particulate matter measuring system, comprising a photometric scattered light unit (1) with a measurement volume (16), wherein the scattered light unit (1) consists of at least one light transmitter (7) which emits (13) light signals, in particular pulsed light signals, and of at least one light-sensitive receiver system (8), which is arranged at at least one angle (15) and which receives the scattered light (14) from the particles (12) forming the particle concentration, characterized in that the scattered light unit (1) with measurement volume (16) is hermetically sealed with the exception of at least one fluid inlet (1*a*) and/or at least one fluid outlet (1*b*), which are provided with blocking devices (2, 3), wherein a sample of the fluid to be examined is applied to the scattered light unit (1) with measurement volume (16) and a predeterminable first number of measurement values is recorded.

19 Claims, 5 Drawing Sheets

Figure 1:
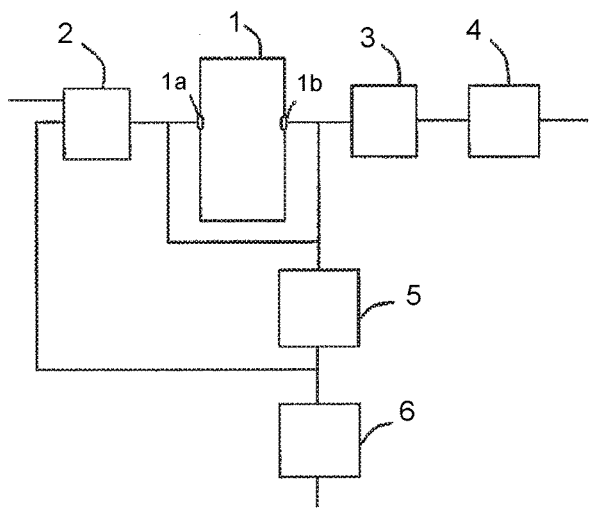

(52) U.S. Cl.
CPC ........... *G01N 2015/0046* (2013.01); *G01N 2015/0053* (2013.01); *G01N 2015/0288* (2013.01); *G01N 2015/0687* (2013.01); *G01N 2015/0693* (2013.01)

(58) Field of Classification Search
CPC ........ G02B 1/06; G02B 26/023; G02B 5/205; G02B 27/00; G02B 27/4233; G02B 27/44; G02B 6/1226; G02B 27/0025; G02B 27/0938; G02B 27/10; G02B 27/1086; G02B 27/12; G02B 27/14; G02B 27/142; G02B 27/146; G02B 27/4272; G02B 5/0221; G02B 5/0268; G02B 5/0284; G02B 5/1814; G02B 5/1823; G02B 5/1838; G02B 5/1861; G01N 2021/95676; G01N 21/3581
See application file for complete search history.

(56) References Cited

U.S. PATENT DOCUMENTS

| | | |
|---|---|---|
| 2006/0144126 A1* | 7/2006 | O'Brien ............ G01N 1/2202 73/23.42 |
| 2013/0248693 A1 | 9/2013 | Buchanan, III et al. |
| 2014/0152986 A1* | 6/2014 | Trainer ............ G01N 15/0205 356/336 |

OTHER PUBLICATIONS

Black, D.L. et al., "Laser-Based Techniques for Particle-Size Measurement: A Review of Sizing Methods and their Industrial Applications", Progress in Energy and Combustion Science, Elsevier Science Publishers, Amsterdam, NL, vol. 22, No. 3, Jan. 1, 1996, pp. 267-306.

* cited by examiner

METHOD AND SYSTEM FOR SIMULTANEOUSLY MEASURING FINE PARTICLE CONCENTRATIONS PM1, PM2.5 AND PM10—PARTICULATE MATTER

BACKGROUND

The invention relates at least to a method for measuring and displaying, in particular simultaneously measuring and displaying, different particle concentrations, in particular particulate matter concentrations, preferably in a flow, using a photometric scattered light unit consisting of a light transmitter which emits light signals, preferably pulsed light signals, into a measurement volume and a light-sensitive receiver system, which is arranged at an angle and which receives the scattered light of the particles which form the particle concentration, wherein the advantageously present through-flow of the fluid to be examined is carried out with a usually right-angled alignment in relation to the light transmission unit and light reception unit.

The invention furthermore relates to apparatuses for simultaneously measuring and displaying different particulate matter concentrations.

Very high particulate matter concentrations are generated in urban and industrial regions as a result of combustion processes. Sometimes, the values are so high (>100 to 200 µg/m³) that a permanent stay in such regions is harmful to health. The cities of Beijing and Shanghai have already been classified as no longer inhabitable regions by the WHO. If attempts are made to accurately measure various particulate matter concentrations, e.g. with a resolution of 1 to 2 µg/m³, it becomes clear that this is linked to very high outlay and costs (€3000 to €30,000). Photometric and gravimetric systems have prevailed. The measurement principles of a scattered light photometer or gravimetric measuring system are already part of the prior art. There are numerous companies, such as Apollo, Honeywell, Sharp, Shinjei et al., which offer OEM sensors on the basis of the scattered light method at relatively low costs (€10 to €20). The accuracy of these OEM sensors lies at approximately 25 to 100 µg/m3. Using this, it is possible to control indoor air purifiers, which start with purification at concentrations of 50 to 100 g/m³ and switch off again at approximately 20 µg/m3. Well-known brands have already equipped indoor air purifiers with such sensors. However, a more accurate, permanently reliable determination of the particulate matter concentration is currently not possible therewith. However, since there is great need for a cost-effective determination of the particulate matter concentrations and in order to protect the health of living beings, a novel cost-effective method for detecting the so-called "particulate matter", abbreviated PM, was developed. Determining PM1.0, PM2.5 and PM10 with mean particle sizes of 1.0 µm, 2.5 µm and 10 µm is conventional. This method not only allows the determination of a fraction such as e.g. the important PM2.5, but also allows the simultaneous determination of a plurality of fractions, such as e.g. PM1.0, PM2.5 and PM10. The resolution threshold of particles lies at approximately 0.3 µm. Using this, even accurate determination of PM0.5 is possible in a safe and reliable manner. An accuracy of a few µg/m³ in the measurement range up to 100 µg/m³ may be obtained therewith.

SUMMARY

The invention is based on the object of highlighting at least one method of the generic type set forth at the outset, by means of which the measurement of various particle concentrations, in particular particulate matter concentrations, is improved. Furthermore, an apparatus for simultaneously measuring and displaying different particle concentrations, in particular particulate matter concentrations, is intended to be highlighted, said apparatus preferably being suitable for carrying out this method. The object is achieved by the methods and by an apparatus with one or more features of the invention. Advantageous embodiments are described below.

In respect of a method, the object is achieved according to the invention in that the stray light unit with measurement volume is hermetically sealed. Here, at least one fluid inlet and/or at least one fluid outlet, which are provided with blocking devices, remain exempt therefrom and remain open within a first step, a sample of the fluid to be examined is applied to the scattered light unit with the measurement volume thereof in a controlled fashion, and a predeterminable first number of measurement values are recorded. The first number of measurement values are recorded repeatedly, in particular continuously, for as long as the measurement is carried out.

Hermetically sealing the scattered light unit prevents unwanted particles from penetrating into the measurement volume through gaps or chinks in the housing of the scattered light unit and contaminating the fluid to be examined there, said fluid to be examined only being able to reach into, or leave from, the scattered light unit via the fluid inlet or outlet in a controlled manner. A very small gap with an aperture of only 10 µm already represents a large opening for particles with a size 1 µm. Such fine particles have a high concentration in the air; 1000 to 10 000 nanoparticles per cubic centimeter are usual. In road traffic, this concentration may rise to 107 per cubic centimeter. Therefore, it is easily conceivable that small particles are able to migrate into the scattered light unit in an uncontrolled fashion, able to dirty the latter on the inside and able to contaminate a sample to be measured if the scattered light unit is not hermetically sealed.

An advantage of this method is also that the scattered light unit may be recalibrated at any time. To this end, a development of the method provides for a virtually particle-free fluid, which was filtered by flowing through a zero filter and which is preferably conveyed by a pump unit, to be introduced into the measurement volume either at the blockable fluid inlet or at the blockable fluid outlet and for a predeterminable first number of measurement values, which are stored as a zero level, to be recorded. Ideally, a zero filter filters out all particles which are larger than gas molecules from the air; actual zero filters filter out at least all particles which are greater than 0.2 µm from the air. A fluid such as air, filtered therewith, may therefore be considered to be particle-free. The pump unit is preferably configured as a diaphragm pump which seals like a stop valve when not in pumping operation. As an alternative thereto, use may also be made of a different pump which is provided with an additional stop valve.

Advantageously, the fluid inlet and fluid outlet may be blocked manually or automatically still before the predeterminable first number of measurement values are recorded and stored as a zero level. However, particularly advantageously, a flow is produced in the scattered light unit for recording the first number of measurement values. This may be carried out by means of a first bypass, the pump unit and an additional stop valve or by means of a second bypass and an additional pump unit. The bypass may be connected over separate valves and lets the fluid circulate.

In a development of the method, the first blocking apparatus and/or second blocking apparatus are opened, the fluid to be examined is applied to the measurement volume and the first blocking apparatus and/or the second blocking apparatus are closed. Advantageously, a flow is also produced here in the scattered light unit which is now completely hermetically sealed again, as a result of which the fluid to be examined can circulate. For the purposes of recording the predeterminable first number of measurement values, it is also advantageous here if this is carried out during the flow. Compared to recording the measurement values in the case of an open fluid inlet and fluid outlet, this development of the method is advantageous in that a fluid sample to be examined may be examined over a longer period of time.

The method according to the invention may be improved further if, particularly when recording the measurement values, the fluid to be examined flows through the scattered light unit at a flow speed that is as constant as possible, preferably by using a suction unit or the pump unit.

Expediently, the method includes the scattered light unit and one or more subsystems being actuated by means of a microprocessor and corresponding measurement data of the light reception unit and further sensors being evaluated and post-processed and the results of the evaluation and/or the post-processing being visualized by means of display units. Such subsystems may include further sensors such as humidity, pressure, flow and gas sensors. The inclusion of the measurement values of these additional sensors in the evaluation may further improve the measurement result from the measurement data of the light reception unit. Moreover, the data of the subsystems may be processed and displayed on a standalone basis.

Actuating the light transmission unit by a microprocessor renders it possible to produce light pulses which are emitted by the light transmission unit and which are freely selectable and adjustable in terms of the pulse width, pulse height and/or pulse frequency. As a result of this, it is possible e.g. to counteract the degradation of the light transmission unit.

A further aspect of the invention, which firstly contributes to improving the above-described method and which secondly also has the potential of improving the measurement of particle concentrations on its own, is expressed by virtue of, in the first number of measurement values, the measurement values being sorted according to their size, in particular increasing from the smallest measurement value to the largest measurement value. Sorting facilitates the use of statistical effects which emerge during an integral measurement of particle concentrations, in which a plurality of particles are situated within the measurement volume during the measurement.

This aspect of the invention has the potential of improving the measurement of particle concentrations on its own, and is accordingly expressed in a method for measuring particle concentrations, in particular particulate matter concentrations, using an optical scattered light particle measuring system comprising a photometric scattered light unit with a measurement volume, wherein the scattered light unit consists of at least one light transmitter which emits light signals, in particular pulsed light signals, and of a light-sensitive receiver system, which is arranged at at least one angle and which receives the scattered light from the particles forming the particle concentration, wherein signals of the light reception unit are captured and, in a first number of captured signals, the associated measurement values are sorted according to their size, in particular increasing from the smallest measurement value to the largest measurement value.

Preferably, a predeterminable second number of measurement values are initially recorded in the above-described methods for the purposes of forming the first number of measurement values. A characteristic value, which may preferably be a maximum or a mean value, is obtained from this predeterminable second number of measurement values of the signals. This characteristic value of the second number of measurement values is then used as one of the measurement values of the first number of measurement values.

Advantageously, in the method according to the invention, at least some of sorted measurement values of the first number of measurement values are combined in at least one freely selectable measurement window which, in particular, is adjustable by software, and assigned to corresponding particle concentrations. By way of example, the $51^{st}$ sorted value is assigned a concentration of 109 μg/m$^3$ if the amplitude value thereof is 650 units while e.g. the $90^{th}$-$93^{rd}$ value is assigned a concentration of 109 μg/m$^3$ if the amplitude value thereof is approximately 700 units.

For the purposes of calibrating the measuring system which is used to carry out the methods according to the invention, the first number of the measurement values is captured at a particle concentration close to zero μg/m3, preferably less than 1 μg/m3. After sorting the first number of measurement values, at least one part thereof is stored as a zero level for a PM value. Moreover, a second part of the sorted first number of measurement values may also be stored as a zero level for the same PM value. However, it is also conceivable to store the measurement values of a plurality of parts of the sorted first number of measurement values as zero level for a plurality of different PM values and thereby undertake a zero calibration of the particle measuring system, in particular particulate matter measuring system. By way of example, at a concentration of 0 μg/m3, the measurement value 600 of the $50^{th}$ and $51^{st}$ value (measurement value number) of the sorted first number of measurement values may be stored as zero level for the PM value of 2.5. Likewise, the measurement value 610 of the $67^{th}$ measurement value number of the sorted values may be stored as zero level for the PM value of 2.5. As an alternative thereto, the measurement value 600 of the $50^{th}$ and $51^{st}$ of the sorted values may also be stored as zero level for the PM value of 1, the measurement value 610 of the $67^{th}$ of the sorted values may be stored as zero level for the PM value of 2.5 and the value 633 of the $95^{th}$ value of the sorted values may be stored as zero level for the PM value of 10.

Here, a PM value or particulate matter value corresponds to the mean size of particles in a particle concentration. Thus, PM0.1 means ultrafine particles (UFP) with a mean size of only 100 nm. Correspondingly, PM1.0, PM2.5 and PM10 represent concentrations of mean particle sizes with 1 μm, 2.5 μm and 10 μm. In this context, the PM values may also be defined in such a way that particle fractions with lower values, i.e. PM1, are contained in the fraction with the respectively higher value, such as e.g. PM2.5, and so PM1 contains particles that are smaller than 1 μm while PM2.5 contains particles that are smaller than 2.5 μm.

In order subsequently to be able to deduce particle concentrations from the measurement values, a dedicated calibration function is set for each PM value, e.g. [measurement value×constant×((2.5 μg/m$^3$)/measurement unit)−zero level]. By way of example, this calibration function may be ascertained by comparison with measurement values from a reference appliance, e.g. a particle counter. By way of example, the current particle concentration for PM2.5 is obtained by calculating the calibration function for PM2.5 by virtue of inserting the $65^{th}$ value of the current measurement into the calibration function if the $65^{th}$ value was assigned the PM value of 2.5 when assigning the PM values.

The PM values are positioned in the sorted arrangement of the current measurement values in such a way that the respective mean particle sizes correlate with the measurement value number. By way of example, it is possible to recognize in FIG. 7 that the measurement value number (X-axis) increases from left to right and, correlating therewith, the mean particle sizes 1.0, 2.5 and 10 likewise increase from left to right.

A particularly accurate calibration is obtained if the particle measuring system may be calibrated by means of monodispersive particle distributions and/or real dust distributions with different particle concentrations, in particular particulate matter concentrations, and new calibration values, such as zero levels, parameters of calibration curves and gravimetric factors, are stored separately, in particular for each PM value.

In a development of the method according to the invention, zero level measurements are repeated from time to time, preferably on a regular basis. The degradation of the scattered light unit is determined by comparison between the current zero levels and preceding zero levels and the particulate matter measurement values are corrected accordingly. The invention also manifests itself in an apparatus for measuring and displaying different particle concentrations, e.g. particulate matter concentrations, which is preferably carried out simultaneously for different PM values. Here, the particle concentrations may be present in a flow consisting of at least two phases. The apparatus comprises a photometric scattered light unit, preferably photometric scattered light unit operated in a pulsed fashion. The scattered light unit consists of at least one light transmission unit which emits light signals, preferably pulsed light signals, and at least one light-sensitive receiver system, which is arranged at one or more angles and which receives the scattered light from the particles. According to the invention, the scattered light unit with measurement volume is initially hermetically sealed with the exception of a fluid inlet and fluid outlet, and the scattered light unit with measurement volume is provided with blocking units at the fluid inlet and fluid outlet, by means of which the fluid inlet and fluid outlet are blockable in a manual or automatic fashion. The hermetic seal is important because particles could otherwise penetrate into the scattered light unit in an uncontrolled manner through available gaps and could dirty the scattered light unit or contaminate the fluid to be examined.

An advantageous effect may be obtained by having optical focusing systems situated in the scattered light unit after the light transmission unit and/or before the light reception unit, the light beams being able to be widened and/or collimated or focused by means of said optical focusing systems. It is likewise advantageous that an optical sump which absorbs the non-scattered light is situated opposite the light transmission unit in the scattered light unit. Further, it is expedient if lasers, semiconductor diodes, white light and/or flashlights are used to emit light signals and photodiodes, phototransistors, photomultipliers and/or photosensitive CMOS chips are used to receive the scattered light.

The invention also relates to an apparatus for measuring and displaying, in particular simultaneously measuring and displaying, different particle concentrations, in particular particulate matter concentrations, preferably in a flow consisting of at least two phases, comprising a photometric scattered light unit, in particular a pulsed photometric scattered light unit, consisting of at least one light transmission unit which emits light signals, in particular pulsed light signals, and at least one light-sensitive receiver system, which is arranged at one or more angles and which receives the scattered light from the particles. This apparatus comprises a control and evaluation unit which is configured to repeatedly record a predeterminable first number of measurement values and to sort the recorded measurement values of the first number of measurement values according to their size, in particular in a manner increasing from the smallest measurement value to the largest measurement value.

BRIEF DESCRIPTION OF THE CLAIMS

Figure 2:
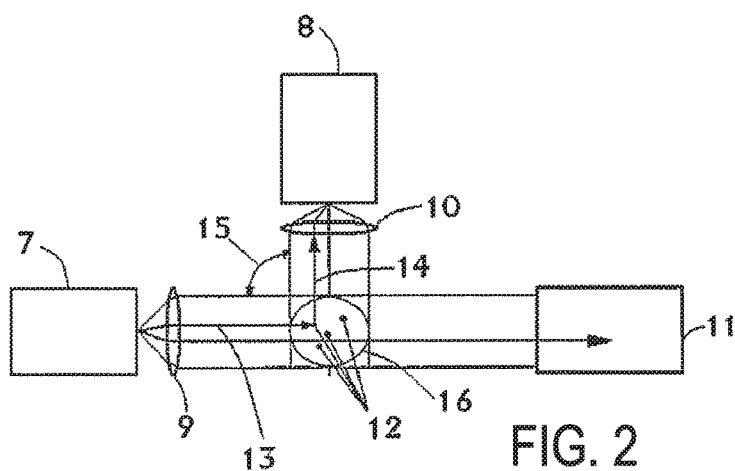
Figure 3:
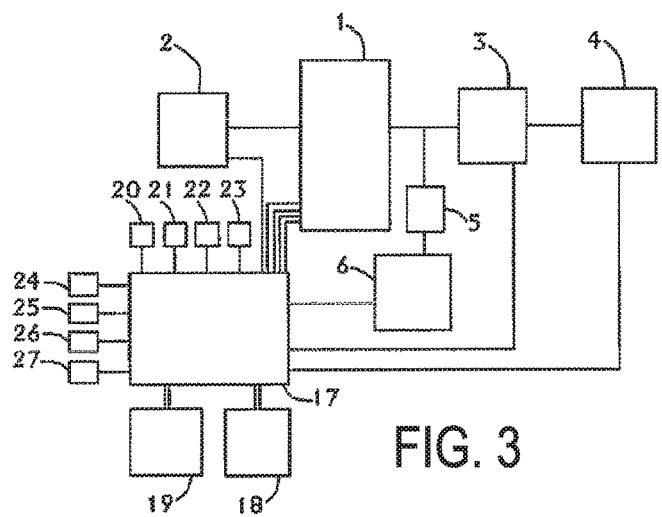
Figure 4:
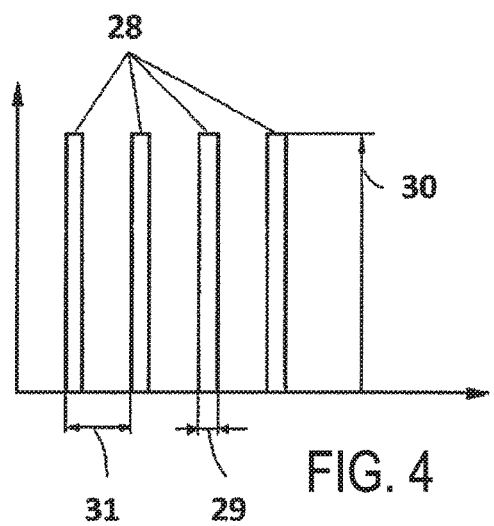
Figure 5:
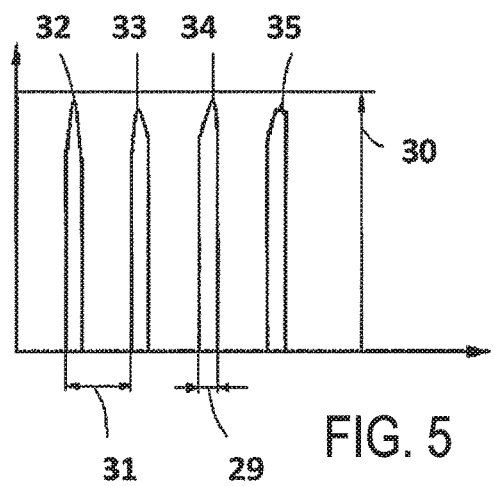
Figure 6:
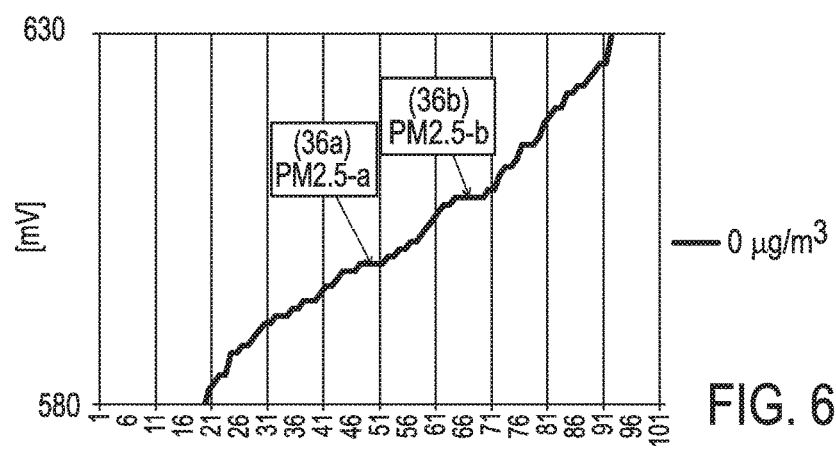
Figure 7:
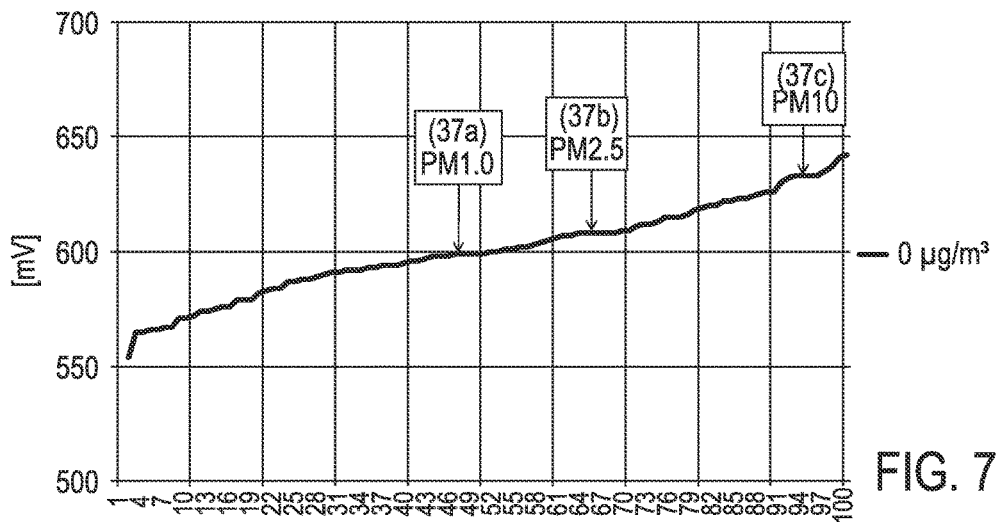
Figure 8:
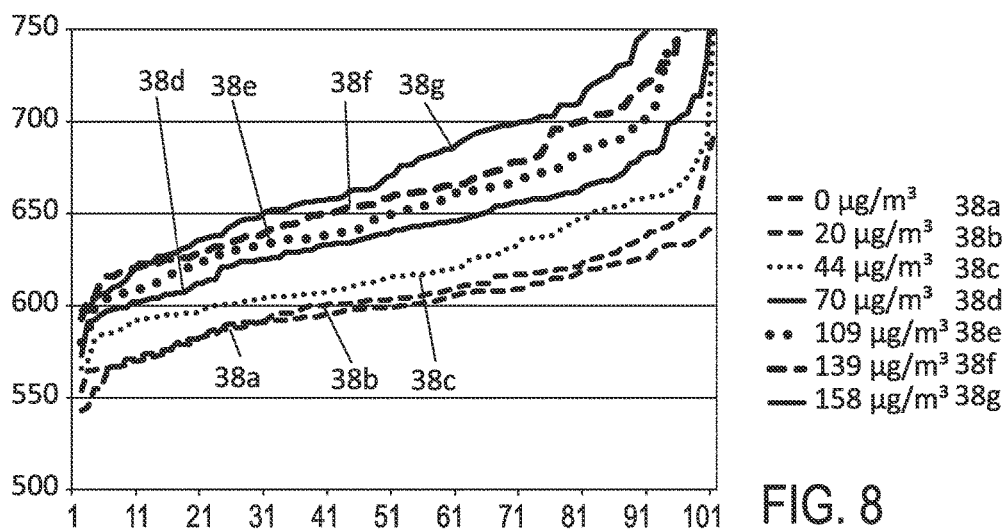
Figure 9:
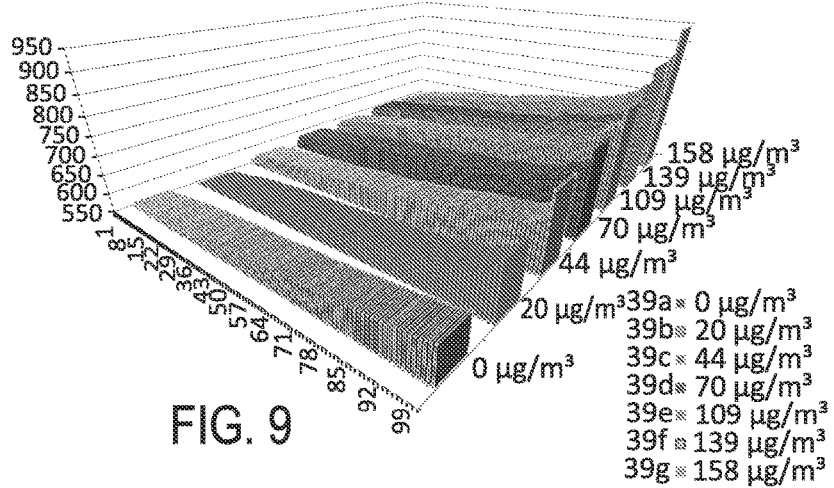
Figure 10:
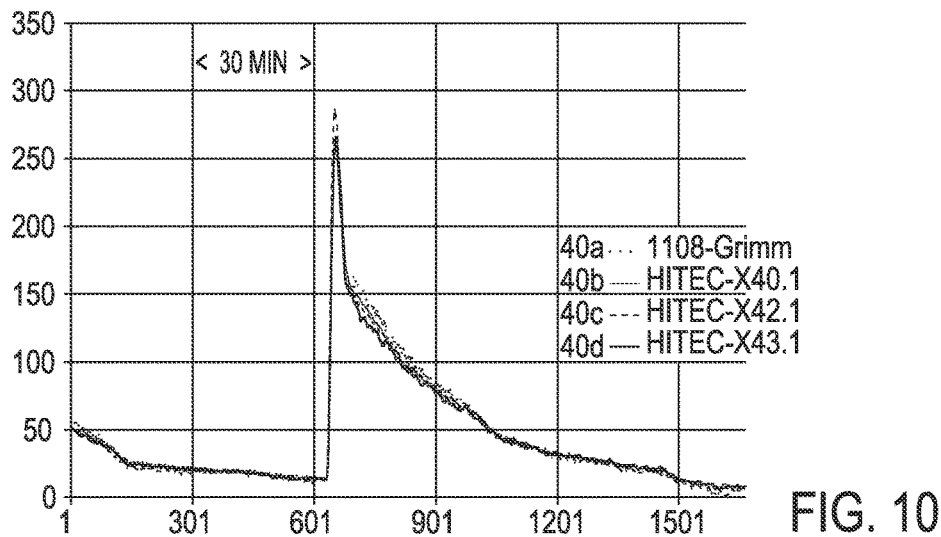
Figure 11:
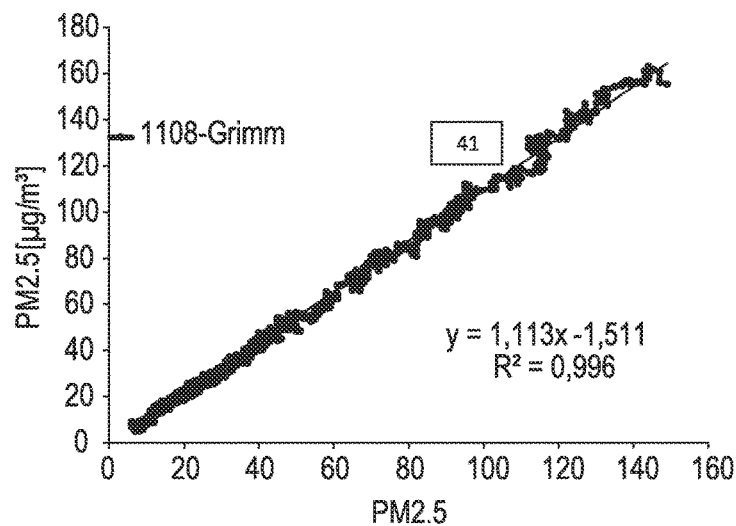
Figure 12:
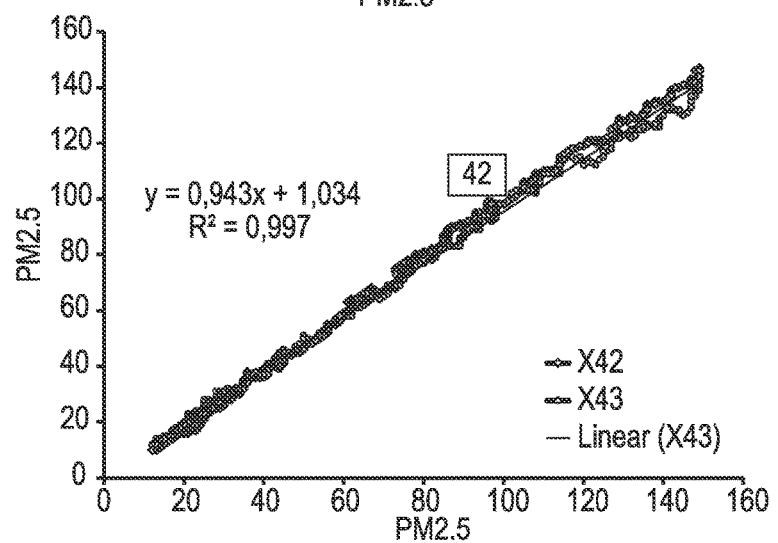
Figure 13:
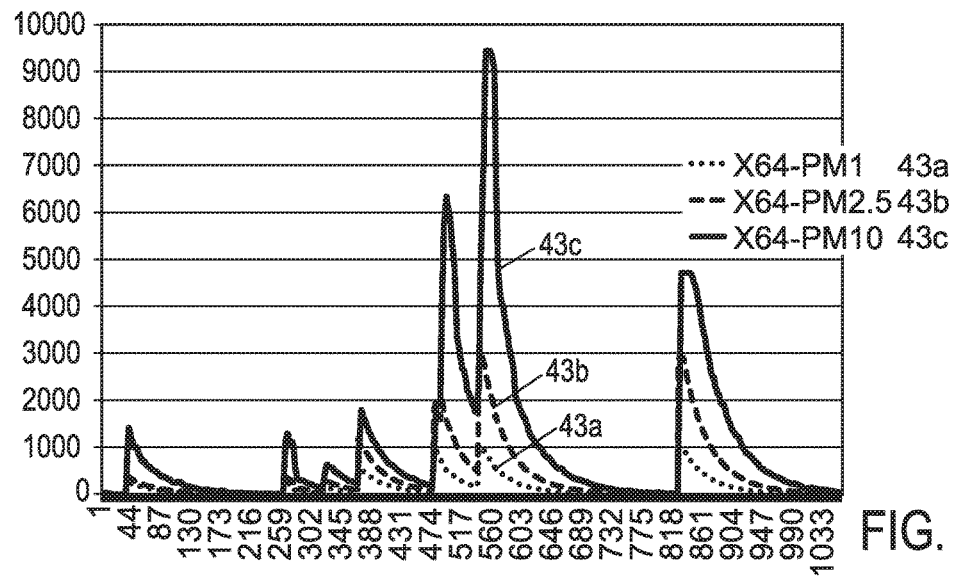
Figure 14:
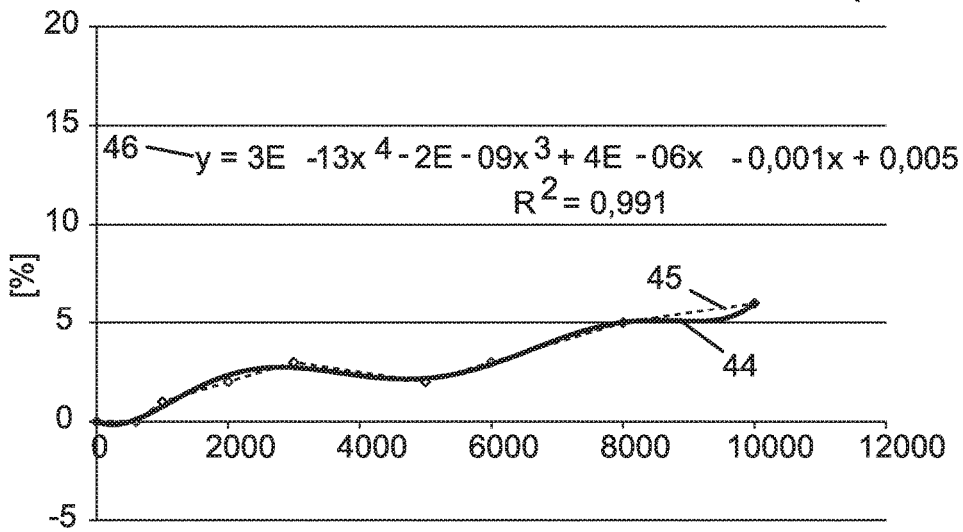
Figure 15:
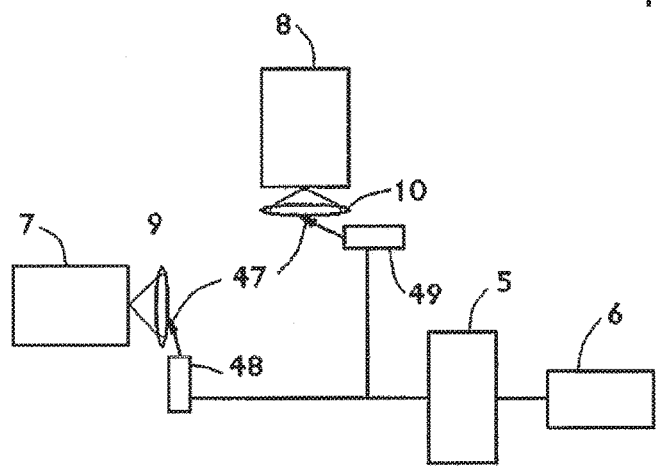

In detail, the figures respectively show:
FIG. 1 shows a schematic overview of the scattered light system.
FIG. 2 shows the optical measuring system comprising transmitter, receiver, light trap and focusing devices.
FIG. 3 shows an extended illustration of FIG. 1 with additional subsystems.
FIG. 4 shows a few light transmission pulses and
FIG. 5 shows the associated reception pulses.
FIG. 6 shows a sorted series of measurement values with assigned PM values.
FIG. 7 likewise shows a sorted series of measurement values with assigned PM values.
FIG. 8 shows sorted measurement series at different particle concentrations.
FIG. 9 shows the same measurement series as in FIG. 8 in a three-dimensional illustration.
FIG. 10 shows a measurement series which was recorded using different measuring appliances in a kitchen, inter alia with a plurality of measuring appliances according to the invention and a highly precise particle counter as a reference appliance.
FIG. 11 shows a straight correlation line for comparing the measuring appliance according to the invention with the reference measuring appliance.
FIG. 12 shows a straight correlation line for comparing two measuring appliances according to the invention among themselves.
FIG. 13 shows the simultaneous measurement of three PM fractions PM1, PM2.5 and PM10.
FIG. 14 shows the measured degradation of a transmission diode in percent in a period of time of up to 10 000 hours.
FIG. 15 shows a measuring system according to the invention in which, additionally, within the system, generated, particle-free fluid, in particular dry air, is guided onto the optical components.

DETAILED DESCRIPTION OF THE PREFERRED EMBODIMENTS

The "particulate matter" measuring system, abbreviated PM measuring system, is depicted schematically in FIG. 1. It consists substantially of a photometric scattered light unit 1 with a preferably round inlet 1a and a preferably round outlet 1b. Initially, the photometric scattered light unit is completely hermetically sealed apart from the inlet 1a and the outlet 1b; this may be carried out by virtue of e.g. adhesively bonding airtight films on gaps and joints. In this measuring system, it is additionally possible to hermetically close off both the inlet by way of an inlet valve 2 and the outlet, which usually lies 180 degrees opposite, by way of an outlet valve 3. Preferably, magnetic valves, which can easily be actuated by a microprocessor, are suitable to this end. However, other valve designs or blocking systems are also suitable. A so-called zero filter 5 has been interposed between outlet valve 3 and outlet of the scattered light unit by means of a T-piece. Ideally, a zero filter filters all particles which are larger than gas molecules from the fluid; actual zero filters at least filter all particles which are greater than 0.2 μm from the fluid. Ambient fluid, in particular ambient air, may be applied to this zero filter by way of an electric pump unit 6. This subsystem is essential for obtaining high accuracy of 1-2 μg/m$^3$ when measuring the PM values. In the case of opened valves, a suction unit 4, preferably a small quiet axial fan, ensures a volumetric flow of, preferably, approximately 1 liter/min through the scattered light unit.

The very accurate measurement method described here preferably starts with a self-test, in which the ambient temperature, humidity, pressure, the temperature of the measuring cell and a so-called zero calibration are carried out before the actual measurements. This system test requires approximately 30 to 60 seconds. Here, a powerful microcomputer preferably queries four measuring sensors which are inserted into the overall system as subsystems. Additionally, the outlet valve 3 is actuated; it seals the inlet of the suction fan 4, which is preferably a quiet axial fan. However, it is also possible to use a small vacuum pump. As a result of the positive pressure in the air lines, the scattered light unit is purged by particle-free air, which preferably has no particles larger than 0.2 μm. In this case, the inlet 1a serves as an outlet. After a short period of time, preferably 20 seconds, the inlet valve 2 is also closed. Now, no particles which are larger than 0.2 μm are situated in the scattered light unit. This low particulate matter concentration, less than 1 μm/m$^3$, now serves as a zero level. Before the measurement method is described in more detail, and the detailed signal processing as well, the photometric system is now described below.

A light transmission unit 7, which emits light at a specific wavelength, e.g. lasers or semiconductor diodes in the wavelength range of 250 to 900 nm, serves as the basis of a scattered light photometer 1, or else white light or a flashlight is also suitable therefor. This light is emitted onto particle-bearing air at a certain angle (FIG. 2: 15), e.g. between 90° and 135° in relation to the light reception unit. If the emitted light is now incident, e.g. as light beam 13, on the surface of the particle 12, a portion of this light is scattered according to the surface and size of said particle and according to the roughness, albedo, shape, diameter etc. thereof. A light reception unit 8 can now be used to detect this scattered light and convert it into an electric signal and amplify the latter for further processing. Optical focusing systems 9 and 10 are situated after the light transmission unit 7 and before the light reception unit. Preferably, simple lenses may also be used. Photodiodes, phototransistors or photomultipliers usually serve as light-sensitive receivers 8. A photosensitive CMOS chip, as is used in many digital cameras, is also suitable to this end. The developed method is suitable for all variants, with a cost-effective photodiode and a phototransistor preferably finding use in this development.

The PM measuring system is depicted schematically in FIG. 3. The core of this system is a powerful microprocessor 17 having several electric inputs and outputs. The corresponding pulses 28 with length 29 and frequency 31 are generated for the light transmission unit by means of pulse width modulation and said pulses are fed to the scattered light photometer 1. The maximum amplitudes are sampled by means of a fast A/D-converter, preferably with a 1 MHz sampling frequency, and the local maximum is determined and stored in a buffer memory by means of a fast sorting routine.

In order to increase the accuracy when determining a particulate matter concentration, a short transmission signal (FIG. 4: 28) or a light pulse (length of approximately 10 to 300 μs; position 29), which is emitted with a high frequency 31 (approximately 0.1 kHz to 0.1 MHz range), is required; as an alternative to this, the reception signal may also be sampled at a high sampling rate. Additionally, a homogeneous fluid flow with a constant volumetric flow rate is expedient. Conventional volumetric flow rates in the measuring cell lie at approximately 1 l/min. The flow velocity in the measuring cell is determined with an accuracy of 1 cm/s and the rotational speed of the suction unit 4 is finely set to the target value by means of a potentiometer. The photosensitive reception unit 8, in this case a cost-effective phototransistor, now receives a number of light pulses with different amplitudes in accordance with the back scattering 14 of the particles 12 at the time of emission and duration of the dwell in the measurement volume 16. The reception pulses 32, 33, 34, 35 in FIG. 5 are not rectangular but have a local maximum at positions which cannot be predicted precisely. However, the accurate capture of the maximum amplitude is advantageous for a precise measurement of the particulate matter concentration. To this end, the amplitude of the received scattered light is sampled repeatedly, preferably 3-5 times, within the transmission time with a length of preferably 10 μs to 300 μs and the maximum is determined, buffer stored and sorted according to size. Each individual pulse per unit time results in an integral information item over all particles (0.3 μm up to >10 μm) which dwelled in the measurement volume 16. These values vary significantly on account of the naturally inhomogeneous particulate matter concentration. It is easy to comprehend that large particles, e.g. a particle with a large size of 10 μm, has about a 100-fold larger back scattering effect than a particle with a small size of 1 μm. However, since usual particulate matter concentrations have inversely proportionally many small particles compared to large particles, a few large and usually many small particles are always captured together within a certain time window. By way of example, if a measurement window of 1 s is selected, 100 amplitude values are obtained in the case of a transmission frequency and sampling frequency of 100 Hz and 300-500 Hz, respectively, said amplitude values now being sorted according to size in this method. A typical sorted distribution is depicted in FIG. 6. Plateaus, such as 36a and 36b, may be identified in FIG. 6 and may be used to set the resolution limit and zero level; by way of example, the zero level in this example is selected at the 48$^{th}$ of the sorted values, corresponding approximately to a sensor offset voltage of 600 mV. This—the offset voltage and the position in the sorted series—is assigned as zero level to a particulate matter concentration, e.g. PM2.5-a. At the same time, the zero level 36b can be assigned to a second plateau, e.g. at the 67$^{th}$ of the sorted values of a second PM2.5-b distribution. Hence, e.g. 100 amplitude values are captured each second. It is possible to further increase the accuracy of the PM2.5 measurement by averaging a plurality of measurement values. Since the natural particulate matter distribution in space is not homogeneous and varies significantly (+/−1-5 μg/m$^3$) in most cases, a calculation of the PM2.5 value by means of a rolling mean of preferably 10 measurement values is expedient. The microprocessor 17 controls an alphanumeric LED display unit 18, preferably with 3-4 digits, by means of which the current measurement value is displayed. Additionally, this microprocessor also controls a light diode unit 19 which actuates and lights up different LEDs in the case of critical particulate matter levels. A traffic light function with the colors green, yellow, red is expediently suitable in this case. In the case of PM2.5 values of up to 24 µg/m$^3$, corresponding LEDs shine in green, the LEDs shine yellow between 25 and 49 µg/m$^3$ and shine red above 50 µg/m$^3$.

In addition to the particulate matter concentration, the microprocessor also determines important environmental data such as ambient temperature, pressure and humidity by means of the corresponding sensors 20, 21, 22. In order to compensate the temperature drift—2 to 4 µg/m$^3$ per degree Celsius of temperature difference are usual—the temperature of the photometer unit 1 is also captured precisely by means of temperature sensor 23. The accuracy is preferably 0.1° C. As a result of a preceding calibration of the temperature response of the measuring electronics and as a result of determining the temperature coefficient, the accuracy of the particulate matter measurement values can be significantly improved, even in a large temperature range, e.g. 10-40° C. Using this, it is possible to realize small temperature drifts of only 0.1 µg/m$^3$ per degree Celsius. The same applies to the influence of the pressure on the fluid volume and the influence of the moisture on the measurement of the particle concentration. Special routines and calibrations allow negative influences as a result of pressure variations or a high humidity to be compensated or at least strongly reduced.

The microprocessor 17 also actuates important interfaces 24, 25, 26, 27. For communication and controlling the microprocessors by means of a terminal program and several software commands, use is preferably made of a USB interface 24. A LAN connector, Wi-Fi or Bluetooth may also be realized for further communication by way of an additional RS232 interface 25 and corresponding commercially available adapters. A further output 26, which is used by a DAC digital-to-analog converter, serves to control appliances such as fans or indoor air purifiers. The offset value and the gradient of the DAC output can be programmed by means of a specific software routine. This is expedient as this allows e.g. an indoor air purifier to be activated automatically in the case of corresponding critical values and to be switched off again when low particulate matter concentrations are reached (energy saving mode). Furthermore, this system moreover has a multichannel analog input 27, by means of which further parameters in respect of the air quality may be determined. By way of these additional sensors, it is possible simultaneously to measure and display e.g. the $CO_2$ concentration and VOC components in the air.

The microprocessor preferably also has an RTC real-time clock, by means of which a timestamp is stored with each measurement, preferably at second intervals. By means of a microSD card—which has several gigabytes of memory—it is possible to store both this time signal and all measurement values in a measurement file. The memory capacity suffices for recording all data over several years.

For larger particulate matter concentrations such as e.g. PM2.5, a plateau at approximately the 65$^{th}$ of the sorted values is preferably selected and the selection is made at approximately the 95$^{th}$ value for large PM10 values. This method now allows both determining individual particulate matter concentrations, such as e.g. only a PM2.5 37b, and simultaneously determining further particulate matter concentrations or particulate matter fractions, such as PM1.0 37a and PM10 37c, this even being in the same measurement window, which is depicted in FIG. 7. If the amplitude values are now averaged around the selected zero offset values such as the 48$^{th}$, 67$^{th}$ and 95$^{th}$ value with plus/minus n-values, preferably 1-5 values, to the left and right thereof, this measure can further increase the accuracy. Since the frequency of 10 µm particles is small in comparison to the particles with the size of 1 µm in the case of a PM10 concentration, it is better, for this application, for the number of the amplitudes to be sorted to be increased by one order of magnitude from preferably a number of 100 to approximately a number of 1000.

In this method, both the number of the PM fractions (1 to 3) to be determined and the positions of the offset values may be selected freely by means of software commands using software. The number of measurement values to be sorted is likewise freely selectable. Preferably, values of 100, 300, 600, 900 and 6000 were selected, corresponding to measurement windows of 1, 3, 6, 9 and 60 seconds. By means of a special software command, the sorted amplitude distribution per measurement window may be output in a matrix. On the basis of this matrix, a check may be carried out as to whether the selected reference values are correct for the zero level. If need be, fine adjustments can still be carried out.

If the particulate matter concentration is now increased, this sorted distribution is shifted accordingly to higher amplitude values (650 mV to 2500 mV); see distributions 38a to 38g in FIG. 8. These 7 distributions embodied in an exemplary manner correspond to PM2.5 levels of 0, 20, 44, 70, 109, 139 and 158 µg/m$^3$. Several distributions were recorded, examined and evaluated in numerous calibration experiments with monodispersive calibration particles with different densities, sizes and forms. A plurality of highly precise absolute aerosol spectrometers running in parallel, such as the appliances 1.107, 1.108 and 1.109 by Grimm, were used as reference instruments. It was possible to show that resolutions of 1 µg/m$^3$ and accuracies when determining e.g. a PM2.5 of less than +/−5 µg/m$^3$ (usually only +/−2 µg/m$^3$) could be obtained in measurement windows with a length from 6 to 60 seconds and at concentrations of less than 100 µg/m$^3$ using this innovative method; see FIG. 10, curves 40a to 40d of real measurements in a kitchen. Accuracies of significantly less than 10% of the readout value were realized for higher concentrations of more than 100 to 10 000 µg/m$^3$. Correlation measurements between these reference appliances and the first prototypes show correlation coefficients of R2 10>0.95, with usual values being around 0.98 and higher; see FIG. 11. In the case of very precise tuning, even 0.996 was reached under real conditions indoors; FIG. 11. The synchronism between a plurality of appliances likewise correlates with values significantly above R2>0.95; see FIG. 12 with R2>0.99. Hence, it was possible for the first time to show that it is also possible to determine particulate matter concentrations under real conditions using a novel measurement method and substantially more cost-effective measurement technology.

The simultaneous measurement of 3 PM fractions PM1 (43a), PM2.5 (43b) and PM10 (43c) was validated in further calibration measurements using dolomite particles, as depicted in FIG. 13.

The laboratory results and measurements under real conditions are very promising. In order to design this measurement method also to have long-term stability and robustness, the degradation of the light transmission unit needs to be taken into account. By way of example, in the case of 100 light pulses per second, a total of, after all, 2.88 million pulses arises per day in the case of 8 hour operation. FIG. 14 plots the measured degradation of a transmission diode (45) in percent over the period of time up to 10 000 hours. It is approximately 6% after 10 000 hours, i.e. after 1250 8-hour days or 10.8 billion pulses. This curve can be approximated very well by means of a $4^{th}$ order polynomial (46). If the operating duration is captured by means of the RTC real-time clock, this effect can be compensated very well over a long period of time—approximately 3.5 years. However, interim calibrations, at the latest after one year (2500-3000 operating hours in the case of an 8-hour day), are usual.

Dirtying of the optical unit (9) and (10) may have a further influence on the accuracy of the measurement system. In order to prevent this, a particle-free shearing flow (47) is applied to the optical units in this system, preferably from slotted nozzles (48 and 49); FIG. 15. The particle-free flow is produced in part by the pump unit (6) with a so-called zero filter 5 disposed downstream thereof. This method reliably prevents gradual dirtying of the optical unit or the lenses since the tiny particles cannot move against this flow. Using this, the optical unit is kept particle-free in a reliable manner. Additionally, the optical unit (9) and (10) may be embodied with a special dust-repellent coating made out of nanoparticles.

The invention claimed is:

1. A method for measuring different particle concentrations using a particle measuring system comprising a photometric scattered light unit (1) with a measurement volume (16), wherein the scattered light unit (1) includes at least one light transmitter (7) which emits pulsed light signals, and at least one light-sensitive receiver system (8), which is arranged at at least one angle (15), the method comprising the at least one light-sensitive receiver system simultaneously receiving scattered light (14) from a plurality of particles (12) forming particle concentrations, the scattered light unit (1) with measurement volume (16) is hermetically sealed with the exception of at least one of a fluid inlet (1a) or a fluid outlet (1b), which are provided with blocking devices (2, 3), applying a sample of the fluid to be examined to the scattered light unit (1) with the measurement volume (16) and recording a predeterminable first number of measurement values, introducing a virtually particle-free fluid, which was filtered by flowing through a zero filter (5) and which is conveyed by a pump unit (6), into the measurement volume (16) either at the blockable fluid inlet (1a, 2) or at the blockable fluid outlet (1b, 3) and recording the predeterminable first number of measurement values, which are stored as a zero level, for calibrating the scattered light unit.

2. The method for measuring particle concentrations as claimed in claim 1, further comprising: capturing signals (32, 33, 34, 35) of the light-sensitive receiver system (8), and in a first number of captured signals, sorting the associated measurement values according to size, and combining at least some of sorted measurement values of the first number of measurement values in at least one freely selectable timed measurement window and assigning them to corresponding particle concentrations.

3. The method for measuring particle concentrations as claimed in claim 2, further comprising obtaining a characteristic value from a predeterminable second number of measurement values of the signals and said characteristic value is used as one of the measurement values of the first number of measurement values.

4. The method as claimed in claim 2, wherein the at least one freely selectable measurement window is adjustable by software.

5. The method as claimed in claim 2, wherein the first number of the measurement values is captured at a particle concentration close to zero $\mu g/m^3$, and at least one part (36a, 36b) of the first number of sorted measurement values is stored as at least one of a zero level for a PM value, (36a, 36b) two equal PM values (36a, 36b) or a plurality of different PM values (37a, 37b, 37c) such as PM1, PM2.5, PM 10 and a zero calibration of the particle measuring system is undertaken thereby.

6. The method as claimed in claim 2, wherein the particle measuring system is calibrated using at least one of monodispersive particle distributions or real dust distributions with different particle concentrations, and new calibration values, including at least one of zero levels, parameters of calibration curves or gravimetric factors, are stored separately for each PM value.

7. The method as claimed in claim 1, wherein the fluid inlet (1a) is blocked manually or automatically by a first one of the blocking devices (2) and the fluid outlet (1b) is blocked manually or automatically by a second one of the blocking devices (3) and a flow of the virtually particle-free fluid is produced in the completely hermetically sealed scattered light unit (1).

8. The method as claimed in claim 7, further comprising opening at least one of the first blocking apparatus or second blocking apparatus, applying the fluid to be examined to the measurement volume (16), closing the at least one of the first blocking apparatus or the second blocking apparatus and producing a flow of the fluid to be examined in the completely hermetically sealed scattered light unit (1).

9. The method as claimed in claim 1, wherein the fluid to be examined flows through the scattered light unit (1) at a flow speed that is constant using a suction unit (4) or the pump unit (6).

10. The method as claimed in claim 1, wherein scattered light unit (1) and one or more subsystems (2, 3, 4, 6, 18, 19, 20, 21, 22, 23, 24, 25, 26, 27) are actuated by a microprocessor (17), corresponding measurement data of the light reception unit (8) and further sensors (20, 21, 22, 23), which constitute parts of the subsystems, are evaluated and post-processed and results of at least one of the evaluation or the post-processing are visualized by display units (18, 19).

11. An apparatus for simultaneously measuring and displaying different particle concentrations in a flow consisting of at least two phases, comprising a photometric scattered light unit (1) including at least one light transmission unit (7) which emits (13) light signals, and at least one light-sensitive receiver system (8), which is arranged at one or more angles (15) and which is configured to simultaneously receive the scattered light (14) from a plurality of particles (12), the scattered light unit (1) with a measurement volume (16) is hermetically sealed with the exception of a fluid inlet (1a) and a fluid outlet (1b) and the scattered light unit (1) with the measurement volume (16) is blockable at the fluid inlet (1a) and the fluid outlet (1b) by blocking units (2, 3) and the scattered light unit (1) comprises at least one of a first bypass or second bypass with a pump unit, and said bypass allows a fluid to be examined to circulate.

12. The apparatus as claimed in claim 11, further comprising optical focusing systems (9, 10) situated after the light transmission unit (7) and before the light reception unit (8), the light beams being able to be at least one of widened, collimated, or focused by said optical focusing systems, and an optical sump (11) which absorbs the non-scattered light is situated opposite the light transmission unit (7).

13. The apparatus as claimed in claim 12, wherein the at least one light transmission unit (7) comprises at least one of lasers, semiconductor diodes, white light or flashlights used to emit light signals (7).

14. The apparatus as claimed in claim 11, further comprising a control and evaluation unit configured to repeatedly record a predeterminable first number of measurement values and to sort the recorded measurement values of the first number of measurement values according to size in a manner increasing from a smallest measurement value to a largest measurement value.

15. The method for measuring particle concentrations as claimed in claim 2, wherein the sorting by size is from the smallest measurement value to the largest measurement value.

16. The method for measuring particle concentrations as claimed in claim 3, wherein the characteristic value is a maximum or mean value (32, 33, 34, 35).

17. The method for measuring particle concentrations as claimed in claim 1, further comprising recording the predeterminable first number of measurement values, which are stored as zero level.

18. The method for measuring particle concentrations as claimed in claim 1, wherein the light transmission unit (7) is actuated by a microprocessor (17) and produces light pulses (28) which are freely selectable and adjustable in terms of pulse width (29), pulse height (30) and pulse frequency (31).

19. The apparatus of claim 13, wherein the at least one light-sensitive receiver system comprises at least one of photodiodes, phototransistors, photomultipliers or photosensitive CMOS chips that receive (8) the scattered light (14, 10).

* * * * *